United States Patent [19]

Lanham et al.

[11] 4,018,652
[45] Apr. 19, 1977

[54] PROCESS AND APPARATUS FOR ASCERTAINING THE CONCENTRATION OF MICROORGANISM IN A WATER SPECIMEN

[75] Inventors: James W. Lanham, St. Louis County; James T. Holen, Florissant; Norman L. Fadler, St. Peters, all of Mo.

[73] Assignee: McDonnell Douglas Corporation, St. Louis, Mo.

[22] Filed: Jan. 9, 1976

[21] Appl. No.: 647,802

[52] U.S. Cl. .................. 195/103.5 M; 23/253 R; 23/259; 195/127; 195/139
[51] Int. Cl.² .................................... C12K 1/04
[58] Field of Search .............. 195/103.5, 127, 139; 23/253 R, 259

[56] References Cited

UNITED STATES PATENTS 3,957,583  5/1976  Gibson et al. .............. 195/103.5 R

OTHER PUBLICATIONS

Martin Frobisher, Fundamentals of Microbiology, 8th Edition, W. B. Saunders Company, 1968, pp. 46–49.

Primary Examiner—Raymond N. Jones
Assistant Examiner—Robert J. Warden
Attorney, Agent, or Firm—Gravely, Lieder & Woodruff

[57] ABSTRACT

The concentration of microorganisms in a known volume of a water specimen is ascertained by introducing the water specimen into a plurality of wells which have known volume and contain a nutrient medium. The mixture of water specimen and nutrient medium is incubated and the wells are observed for a change in the appearance thereof which indicates metabolic activity, that is, the existence of microorganisms in the wells. If all the wells change appearance, then it is known that the concentration exceeds a certain limit, that is, at least one cell per specific well volume. On the other hand, if none of the wells change, then it is most likely the concentration is less than one cell per total volume of specimen in the wells. A change in appearance of some but not all of the wells indicates a concentration between the foregoing limits, and this concentration is estimated by statistical evaluation based on proven statistical computations.

7 Claims, 10 Drawing Figures

U.S. Patent  April 19, 1977  Sheet 1 of 2  4,018,652
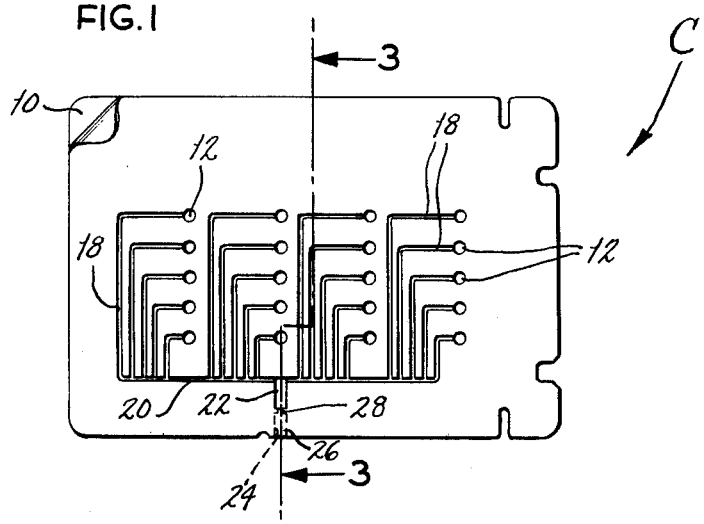
FIG. 1
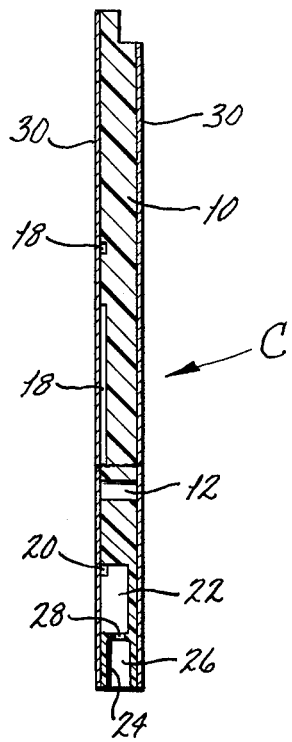
FIG. 3
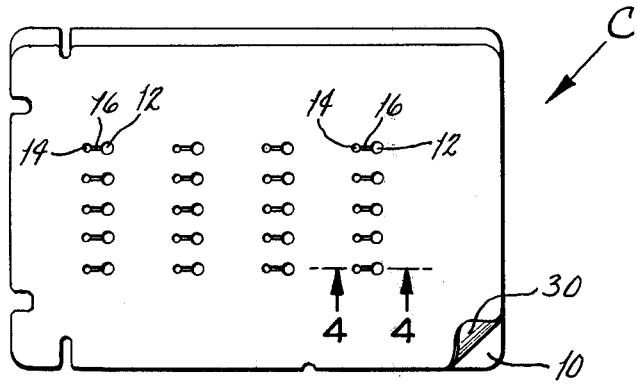
FIG. 2
FIG. 4
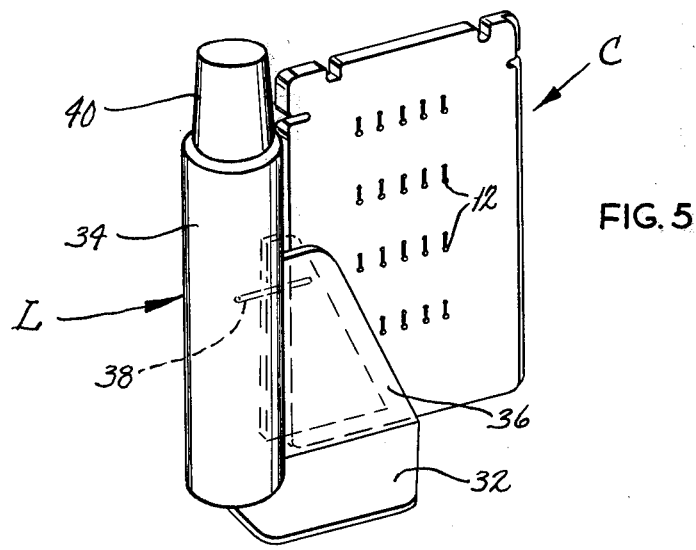
FIG. 5

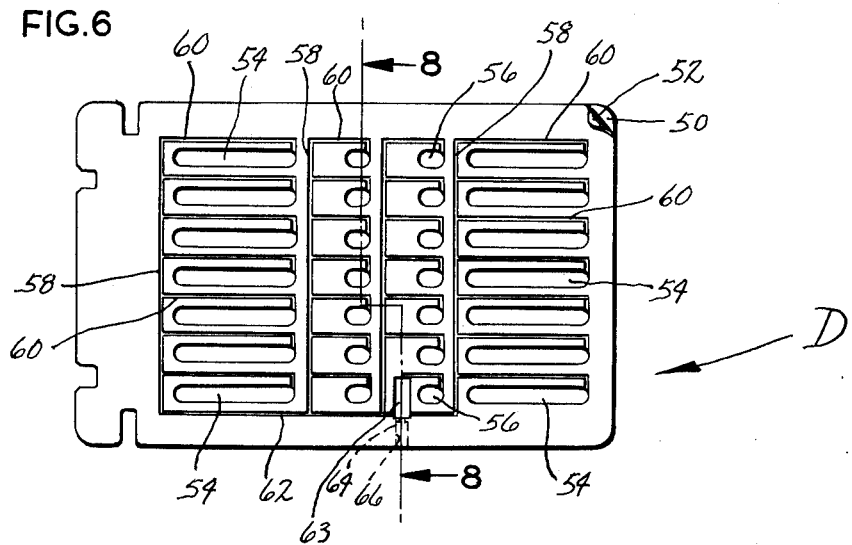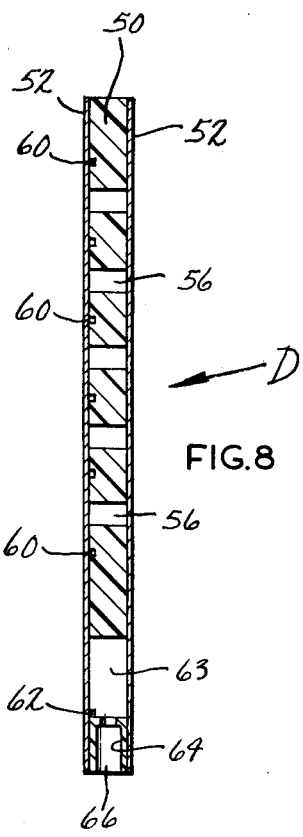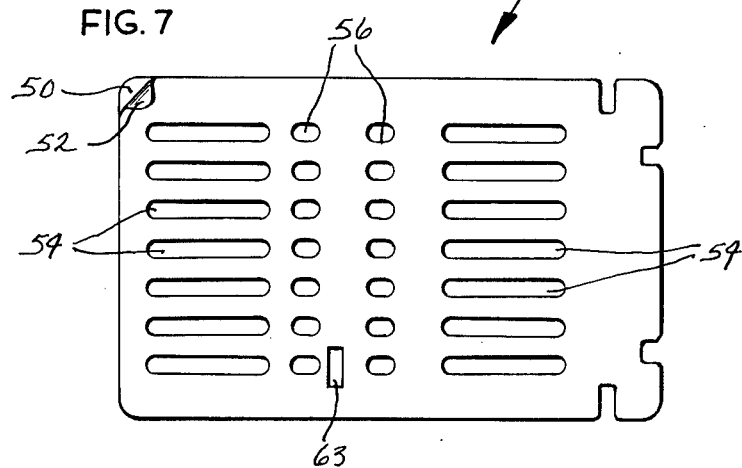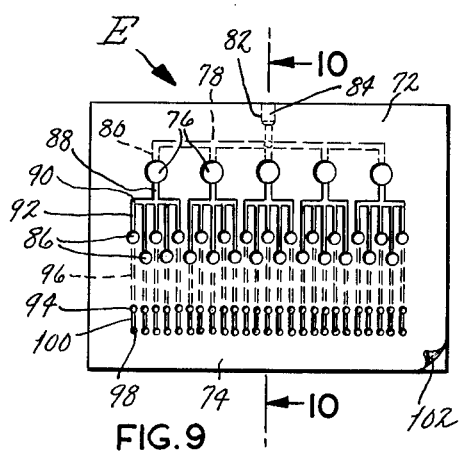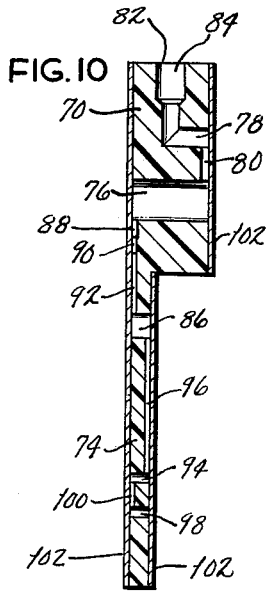

PROCESS AND APPARATUS FOR ASCERTAINING THE CONCENTRATION OF MICROORGANISM IN A WATER SPECIMEN

BACKGROUND OF THE INVENTION

This invention relates in general to microorganisms and more particularly to a process and apparatus for enumerating microorganisms in a water sample.

Contamination of public waters such as streams, rivers and lakes by residential and industrial sewage constitutes a major environmental problem, since such waters are the primary source of drinking water and the water used for the preparation and processing of foods, drugs and cosmetics. Moreover, such bodies of water represent a principal source of recreation. While the solution to the contamination problem of course involves eliminating harmful microorganisms from effluents which enter such bodies of water; it also requires continuous microbiological monitoring of the effluents as well as the public waters themselves. Current techniques for microbiological analysis are time-consuming, laborious and expensive.

There are two widely practiced procedures for ascertaining the bacterial count of water or aqueous suspensions. The first, commonly called the Most Probable Number, or MPN procedure, requires serial 10-fold dilutions of a sample into a nutrient medium with each successive dilution usually being 1 ml. of the previous dilution mixed into 9 ml. of nutrient medium. The microorganisms are then allowed to grow and the various dilutions are observed for turbidity, change of color, or some other indication of growth. The reciprocal of the next to the last dilution showing growth is taken as the concentration in cells per milliter.

In the second procedure cells are collected on a membrane filter, and the filter is placed either on an absorbent pad saturated with culture media, or on solid media containing bacteriological agar. The cells are visualized as colonies on the membrane filter after a defined period of incubation and the number of colonies, related to the dilution used and amount filtered, provides the number of cells in the original sample. This procedure is commonly called the membrane filter process.

Since the membrane filter procedure is limited to samples which will not clog the membrane pores, and is not effective when chlorinated samples are tested, the MPN procedure has become the most widely accepted procedure for determining bacterial counts in water.

In its simplest form, the MPN procedure involves a straight 10-fold dilution to extinction using a single set of test tubes. Measured aliquots of these dilutions are then added to tubes containing nutrient medium. For example, the first dilution tube will contain 10 ml. of sample without any dilution ($10^0$ dilution). The second dilution tube will contain 1 ml. of sample and 9 ml. of diluent ($10^{-1}$ dilution). The third dilution tube will contain 0.1 ml. of sample in 9.9 ml. of diluent ($10^{-2}$ dilution). The fourth, fifth, etc. dilution tubes are filled with 9 ml. diluent and 1 ml. of suspension derived from their immediate predecessors in the series. Thus, the concentration of sample in the fourth dilution tube will be 1/1000 that of the original sample ($10^{-3}$ dilution), while the concentration in the fifth dilution tube will be 1/10000 that of the sample ($10^{-4}$ dilution).

One ml. aliquots of each dilution tube are then added to corresponding tubes containing nutrient medium (culture tubes), thus resulting in a series of tubes. The first culture tube of this series will contain 1.0 ml. of the $10^0$ dilution, the second tube 1.0 ml. of the $10^{-1}$ dilution, and so on to a final tube containing 1.0 ml. of the $10^{-5}$ dilution. These culture tubes are then incubated and observed for changes. If the fifth culture tube (which received 1.0 ml. of the $10^{-5}$ dilution) is the last to exhibit growth, then at least one cell was present in the 1 ml. derived from the $10^{-5}$ dilution of the dilution tube and added to the fifth culture tube. It is assumed, therefore, that each ml. in the sixth dilution tube contained one cell also, or a concentration therein of one cell/ml. Since this dilution constitutes 1/100,000 of the $10^0$, or $10^{-5}$, then the concentration in the $10^0$ sample is the reciprocal of $10^{-5}$ which is $10^5$ cells per ml.

A single series of tubes gives only a rough estimate. To provide greater accuracy, usually 5 tubes of each dilution are employed. Under normal circumstances not all of the series will dilute to extinction at the same dilution. For example, three of the tubes of $10^{-4}$ dilution may show growth, while the two remaining do not. Tables prepared from statistical evaluations are available to provide the bacteria count for any combination of growth and no growth tubes at various dilutions. Of course, the greater the number of series, the more accurate is the count.

From the foregoing, it is quite apparent that the MPN method with all its dilutions of dilutions, is quite laborious and time-consuming and requires a considerable amount of culture medium.

SUMMARY OF THE INVENTION

One of the principal objects of the present invention is to provide an apparatus and method for enumerating microorganisms within a sample in a relatively short time and with a minimum amount of effort. Another object is to provide an apparatus and method of the type stated which does not rely on or require a large number of serial dilutions for enumeration, nor does it require the user to prepare media. A further object is to provide a process of the type stated which is highly aseptic so that it is not easily subjected to contamination or rendering false positives from such contamination. An additional object is to provide an apparatus and process of the type stated which may be used to enumerate specific groups of microorganisms such as fecal streptococci, coliforms, aerobes and anaerobes, or even individual genera such as Esherichia, Klebsiella, Enterobacter, Pseudomonas and Proteus. Still another object is to provide a process and apparatus of the type stated which is ideally suited for preforming bacterial counts of water derived from lakes, rivers, streams and the like or from the effluents of sewage treatment plants which discharge into such bodies. These and other objects and advantages will become apparent hereinafter.

The present invention is embodied in a process including obtaining a liquid specimen, filling a plurality of cavities of known volume with the specimen, mixing the specimen in the cavities with a nutrient medium, and observing the cavities for a change in the appearance thereof to determine the number of cavities which change appearance. The invention also resides in an apparatus for performing the foregoing process, that apparatus having a plurality of wells of equal volume. The invention also consists in the parts and in the arrangements and combinations of parts hereinafter described and claimed.

DESCRIPTION OF THE DRAWINGS

FIG. 1 is a plan view showing the top of a cassette used in the process of the present invention;

FIG. 2 is a plan view showing the bottom of the cassette;

FIG. 3 is a sectional view taken along line 3—3 of FIG. 1;

FIG. 4 is a fragmentary sectional view taken along line 4—4 of FIG. 2 and showing one of the viewing wells in the cassette and its associated overflow chamber and filling channel;

FIG. 5 is a perspective view showing the cassette of FIGS. 1–4 being loaded with a liquid specimen in a loading device;

FIG. 6 is a top plan view of a modified cassette containing 28 wells;

FIG. 7 is a bottom plan view of the modified cassette of FIG. 6;

FIG. 8 is a sectional view taken along line 8—8 of FIG. 7;

FIG. 9 is a plan view of still another modified cassette containing 55 wells; and FIG. 10 is a sectional view taken along line 10—10 of FIG. 9.

DETAILED DESCRIPTION

Referring now to the drawings (FIGS. 1 and 2), C designates a cassette used in the process of the present invention for enumerating microorganisms in a water sample such as might be derived from a lake, river, stream or other body of water or from the effluent of a sewage treatment or industrial plant. The cassette C is rectangular in shape, measuring about 2.5 inches by 3.5 inches and is about 0.125 inches thick.

The cassette C includes (FIGS. 1–4) a rigid transparent plate 10, which is preferably formed from a suitable plastic such as polycarbonate and is the same size and shape as the cassette C. The plate 10 has 20 viewing wells 12 arranged in four transverse rows of five each. Each viewing well 12 extends completely through the plate 10 (FIGS. 3 and 4), that is, from one major surface area to the other, and is of known volume which may be virtually any desired volume, depending on the size of the cassette C. Volumes from 0.005 ml. to approximately 0.10 ml. are representative. All of the wells 12 are of equal volume. Located adjacent to each well 12 is an overflow chamber 14 (FIGS. 2 and 4), and these chambers 14 extend only partially through the plate 10 and hence open out of only one of the two major surface areas. Each overflow chamber 14 is connected to its adjacent viewing well 12 through shallow connecting channels 16 which likewise opens out of the same surface area as the overflow chambers 14. The overflow chambers 14 assure complete filling of the wells 12.

The plate 10 further has separate filling channels 18 (FIGS. 1 and 3), leading to each of the viewing wells 12 from a longitudinally extending feeder channel 20 which in turn is located close to one of the longitudinal edges of the plate 10. The filling and feeder channels 18 and 20 are quite shallow and open out of the opposite major surface of the plate 10, that is, the surface opposite from which the overflow chambers 14 and connecting channels 16 open. Each filling channel 18 is of a dog leg configuration.

Approximately, midway between its ends the feeder channel 20 opens into a short inlet channel 22 (FIGS. 1 and 3) which likewise opens out of the same surface area on the plate 10 as does the feeder channel 20, but the inlet channel 22 is of substantially greater depth, extending almost all the way through the plate 12. The inlet channel 22 projects laterally from the feeder channel 20 and aligns with a bore 24 which opens out of the adjacent longitudinal edge of the plate 10. The bore 24 contains a tightly fitted septum 26 formed from a suitable elastomeric material and is connected with the inlet channel 22 through a short connecting bore 28 of reduced diameter.

Each viewing well 12 contains a culture medium which is preferably in a dehydrated condition. The medium may be a universal medium in the sense that it sustains and responds to practically all microorganisms. On the other hand, it may be a selective medium which will both sustain and respond to only a selected species or group of microorganisms. The response should be such that the mixture of culture medium and water will exhibit a change in appearance or light transmitting characteristics when a microorganism capable of triggering the culture medium is present. Thus, in the case of a universal medium practically all microorganisms will effect a change in appearance. On the other hand, where a selective medium is present, only the microorganism to which the medium is specific will cause a change in appearance. Suitable selective media are disclosed in U.S. patent application Ser. No. 461,249 of Clifton Aldridge, Jr. et al which was filed Apr. 16, 1974 and is entitled PROCESS AND APPARATUS FOR ANALYZING SPECIMENS FOR THE PRESENCE OF MICROORGANISMS THEREIN, now U.S. Pat. No. 3,963,355.

The two major surface areas of the plate 10 are covered with transparent tapes 30 (FIG. 3) which are wide enough to cover the wells 12. Thus, the two tapes 30 close the ends of the wells 12 and retain the culture medium in them. The one tape 30 further covers the overflow chambers 14 and connecting channels 16, while the other tape 30 further covers the inlet channel 22, the feeder channel 20, and the filler channels 18. Hence, the tapes 30 together with the septum 28 completely isolate the interior of the cassette C, that is, the inlet channel 22, the feeder channel 20, the filling channels 18, the wells 12, the connecting channels 16, and the overflow chambers 14 from the surrounding atmosphere, and since the culture medium is in the wells 12, it is likewise isolated and protected from contamination. The tape 30 is slightly permeable in the sense that it will admit air to the wells 12, but the permeability is such that neither water nor microorganisms can escape from the wells. Furthermore, the tapes 30 admit air to the wells 12 so slowly that they permit the interior of the plate 10 to be placed under a vacuum of at least 28 inches Hg and held at that condition for at least 3 minutes. FEP 5430 tape marketed by the 3M Company is suitable for the tapes 30.

The cassette C is loaded with a water specimen in a loading device L (FIG. 5) including a flat base 32, a tube 34 projecting upwardly from the base 32, and a pair of parallel guide webs 36 interposed between the base 32 and the tube 34. The spacing between the webs 36 is slightly greater than the thickness of the cassette C so that the cassette C may be fitted between them. The tube has a hollow needle 38 projected radially from it into the space between the webs 36 and the distance between this needle 38 and the base equals the distance between one of the transverse edges on the cassette C and the bore 24 containing the septum 26. Hence, when the cassette C is inserted between the webs 36 with its transverse edge resting on the base 32, the needle 38 will align with the septum 26. To couple the cassette C with the loading device L, the cassette C is advanced toward the tube 34 until the needle 38 is projected through the septum 26. This provides communication between the interior of the tube 34 and the interior of the cassette C. The upper end of the tube 34 is open and is fitted with a flexible stack 40 which serves to connect the tube to a vacuum line (not shown), and that vacuum line is evacuated by means of a vacuum pump.

To estimate the bacterial count in a known volume of specimen using the cassette C, the cassette C is first coupled with the loading device L such that the needle 38 on the tube 34 of the loading device L is projected through the septum 26 of the cassette C. This places the interior of the cassette C, that is, the inlet channel 22, the feeder channel 20, the filling channels 18, the viewing wells 12, the connecting channels 16 and the overflow chambers 14, in communication with the interior of the tube 34. Next, the tube 34 is filled with the water specimen. The tube 34 is large enough to receive the total volume of specimen.

Once the tube 34 is filled with the specimen, the flexible stack 40 thereon is connected with a vacuum line and a vacuum of at least 28 inches Hg is created. As a result, the air formerly trapped in the interior of the cassette C passes out of the cassette C through the needle 38 and bubbles through the water specimen in the tube 34, thus, establishing the vacuum in the interior of the cassette C also. In this regard, it will be recalled that the permeability of the tapes 30 is such that the vacuum is maintained for at least the time required to develop it.

After the desired vacuum is established in the tube 12 and cassette C connected thereto, that vacuum is released by venting the upper end of the tube 34 to the surrounding atmosphere. The resulting force developed on the water specimen within the tube 34 by the atmosphere forces the water specimen into the cassette C. In particular, the water specimen flows in order through the inlet channel 22, the feeder channel 20, the filling channels 18, the viewing wells 12, the connecting channels 16 and the overflow chambers 14. In other words, the water specimen replaces the air evacuated from the cassette C. Any air which is not evacuated accumulates in the overflow chambers 14. The water upon entering the viewing wells 12 rehydrates the culture medium therein. Bacteria in the water sample are thus randomly separated into the wells 12.

Once the cassette C is filled, it is withdrawn from the loading device L and the septum 26 seals, isolating the interior of the cassette C from the surrounding atmosphere. The cassette C is then incubated at the desired incubation temperature for about 12 to 18 hours. At the end of the time the viewing wells 12 are observed to determine how many exhibit a change in light transmitting characteristics which is a manifestation of growth or more accurately metabolic activity. Of course, if the medium is a universal medium any microorganism will trigger the change. On the other hand, if it is a selective medium, only the species or group of microorganisms to which the medium is specific will cause the change in light transmitting characteristics.

Since the volume of each viewing well 12 is known, the number of microorganisms in the specimen may be ascertained as falling beyond or within certain limits. Assuming that each of the 20 viewing wells has a volume of 0.1 ml., then if all of the wells 12 exhibit growth it is most likely that the concentration of microorganisms in the specimen is greater than one cell or microorganism per 0.1 ml. or greater than 10 cells per ml. On the other hand, if none of the wells 12 show growth, then it is most likely that there is less than one cell or microorganism in every 2.0 ml. (the total volume of the 20 wells 12) or 0.5 cells per ml. Thus, the cassette C and its associated process is suitable for use by one seeking to determine if the bacteria count is less than or in excess of certain specified limits, those limits being 10 cells per ml. and 0.5 cells per ml. in the foregoing example. The example assumes perfect random distribution throughout the cassette C. Actually, the numerical limits are only arithmetic approximations. More accurate estimations may be established statistically. When considered statistically, the lower limit is about the same at 0.5 cells per ml., but the upper limit rises to 30 cells per ml. (see Table A).

When some but not all of the wells 12 exhibit growth it is reasonable to assume that the bacteria count falls somewhere between the statistical limits established for the cassette C, which in the foregoing example is somewhere between 0.5 cells per ml. and 30 cells per ml. Statistical evaluations similar to Most Probable Number charts may be used to estimate the number of cells in the range with reasonable accuracy. With reference to the previously discussed example, statistical evaluations in the form of a table (see Table A) show that when 13 of the 20 wells 12 exhibit growth, the bacterial count is about 10.5 cells per ml.

Still more latitude is acquired by running several tests each in separate cassettes C and with different dilutions of the specimens. In the example given above an initial 1/10 dilution of the specimen would adjust the statistical upper limits of the range to 300 cells per ml., while a 1/100 dilution would adjust the upper limit to 3000 cells per ml. The lower limit would remain the same at 0.5 cells per ml. Thus, the cassette C makes it a relatively simple matter to determine if the bacterial count exceeds a specified limit.

Greater latitude may also be obtained by using separate cassettes C provided with wells 12 of different volume. For example, the one cassette C may have 0.1 ml. wells 12, and the next might have 0.01 ml. wells 12.

EXAMPLE NO. 1

Each of the three cassettes C contained 20 wells 12 and each well 12 had a volume of 0.1 ml. Moreover, the culture medium in each well 12 was specific to the fecal coliform group of organisms. That group is one of the most significant insofar as public waters are concerned, since its concentration provides a good indication of the suitability of such water for drinking, recreational, and other purposes. The first cassette C1 was loaded with a water specimen derived from a cooling fountain; the second cassette C2 was loaded with a specimen derived from a creek; and the third cassette C3 was loaded with a specimen acquired from a sewage treatment lagoon.

After incubating the cassettes C for 12 to 18 hours, none of the wells 12 of the cassette C1 exhibited a change in the light transmitting characteristics thereof, thereby indicating that the fecal coliform count in the cooling fountain water was less than 0.5 cells per ml. The cassette C2 containing the creek water had 14 wells 12 which showed growth, while the remaining did not. From the statistical table below it was determined that the fecal coliform count approximated 12 cells per ml. The cassette C3 had growth in all wells 12, indicating that the fecal coliform count exceeded 30 cells per ml.

TABLE A

For a 20 well cassette, each well being 0.1 ml.

| Wells Positive | Most Probable Number Count (cells/ml.) |
| --- | --- |
| 0 | <0.5 |
| 1 | 0.51 |
| 2 | 1.05 |
| 3 | 1.60 |
| 4 | 2.20 |
| 5 | 2.90 |
| 6 | 3.55 |
| 7 | 4.30 |
| 8 | 5.10 |
| 9 | 6.00 |
| 10 | 6.95 |
| 11 | 8.00 |
| 12 | 9.15 |
| 13 | 10.50 |
| 14 | 12.00 |
| 15 | 13.85 |
| 16 | 16.00 |
| 17 | 19.00 |
| 18 | 23.00 |
| 19 | 30.00 |
| 20 | >30.00 |

EXAMPLE NO. 2

Three cassettes C of the same type and volume as described in Example 1 were employed. However, the first cassette C1 was loaded with a specimen acquired from a sewage treatment lagoon. The second cassette C2 was loaded with a 10-fold dilution of the same sample, while the third cassette C3 was loaded with a 100-fold dilution of the same sample. After a 12-18 hour incubation at 35° C. the following results were obtained. The first cassette C1 showed 20 positive wells 12, indicating a concentration of greater than 30 cells per ml. The second cassette C2 also showed 20 positive wells 12 indicating a concentration in the original sample of greater than 300 cells per ml., since only a 10-fold dilution was loaded into that cassette. The cassette C3 showed 9 positive wells 12. From Table A 9 positive wells correspond to 6.0 cells per ml. But since a 100-fold dilution was loaded into the cassette C3, the Figure must be multiplied by 100 to give the cell concentration in the original sample, which would be 600 cells per ml.

MODIFICATION

A modified cassette D (FIGS. 6–8) differs from the cassette C in that it provides its own 10-fold dilutions. The cassette D possesses substantially the same external configuration as the cassette C and likewise has a rigid plastic plate 50 covered on both of its major surface areas by transparent tapes 52 (FIG. 8).

The plate 60 contains 14 large wells 54 and 14 small wells 56, with the latter being 1/10 the volume of the former. The large wells 54 are elongated in the direction of the longitudinal axis of the plate 50 and are arranged in two rows at the end of the plate 50. The small wells 56 are likewise arranged in two rows, those rows being between the rows of large wells 54. Both the large wells 54 and the small wells 56 extend completely through the plate 50, their ends being closed by the tapes 52. The large wells 54 may have a volume of 0.180 ml. and the small wells a volume of 0.0180 ml.

Extended along the ends of the wells 54 and 56 in each row transverse feeder channels 58 (FIG. 6) which are connected to the individual wells 54 and 56 through separate filling channels 60. All but one of the transverse feeder channels 58 connect with a longitudinal feeder channel 62 which intermediate to its ends opens into an inlet cavity 63. The one feeder channel 58 which does not connect with the channel 62, opens directly into the inlet cavity 63. The cavity 63 in turn communicates with a bore 64 having a septum 66 fitted therein. The channels 58, 60 and 64 open out of the plate 50 through one major surface area thereof, and these outwardly opening sides of the channels 58, 60 and 64 are covered with one of the tapes 52. All of the viewing wells 54 and 56 contain a dehydrated nutrient medium which may be universal or selective.

The cassette D is coupled with the loading device L and filled with a water specimen in the same manner as the cassette C. Once filled, the cassette D is incubated at 35° C. for 12 to 18 hours. Then it is observed to determine the number of large wells 54 and the number of small wells 56 which exhibit growth.

Assuming the purposes of illustration that the large wells 54 are 0.180 ml. and the small wells 56 are 0.0180 ml., and that all of the wells 54 and 56 exhibited growth, then it is certain that the concentration of microorganisms is greater than one cell per 0.0180 ml. or 55.5 cells per ml. when considered arithmetically and 146 cells per ml. when considered statistically (see Table B). On the other hand, if none of the wells 54 and 56 show growth, then most likely there is less than one cell per 2.772 ml. (the total volume of all the wells 54 and 56) or 0.36 cells per ml. For varying combinations of growth and no growth in both the large wells 54 and the small wells 56, tables based on proven statistical computations are referred to (see Table B).

The presence of the two sets of wells 54 and 56 having different volumes considerably extends the range of concentration over which the cassette D is functional. Without dilution the range extends from 0.36 to 146 cells per ml. With a 1/10 dilution the range extends from 0.36 to 1460 cells per ml.

EXAMPLE NO. 3

Three specimens of water were obtained, one from a cooling fountain, another from a creek, and still another from a sewage treatment lagoon. The specimens from the fountain and creek were loaded into cassettes D1 and D2 directly, while the specimen from the lagoon was diluted 10 fold and loaded into the cassette D3. The wells 54 and 56 of these cassettes D1, D2 and D3 contained a universal nutrient medium.

After incubation at 35° C. for 12 to 18 hours, all of the wells 54 and 56 of the cassette D3 (lagoon) exhibited growth indicating that one cell existed for each 0.0180 ml. or that the concentration was in excess of 146 cells per ml. of diluted specimen when considered statistically. Since the specimen was originally diluted to 10 times its original volume, the actual concentration was in excess of 1460 cells per ml. of undiluted specimen.

In the cassette D2 containing the creek specimen, all of the large wells 54 exhibit growth but only 7 of the small wells 56 did so. From the following Table B prepared from statistical evaluations, it was determined that the actual cell count was 39.01 cells per ml. In the cassette D1 containing the fountain specimen, only three of the large wells 56 exhibited growth, while none of the small wells 54 did so. From Table B it was determined that the concentration of microorganisms in the specimen was 1.2 cells per ml.

TABLE B
For a cassette containing 14 wells of 0.18 ml. and 14 wells of 0.018 ml.

| Number Positive | | | Number Positive | | |
|---|---|---|---|---|---|
| 0.18 ml | 0.018 ml | MPN (cells/ml) | 0.18 ml | 0.018 ml | MPN (cells/ml) |
| 0 | 0 | <.36 | 8 | 0 | 4.07 |
| 1 | 0 | 0.37 | 8 | 7 | 8.26 |
| 1 | 7 | 3.06 | 8 | 14 | 13.26 |
| 1 | 14 | 5.90 | 9 | 0 | 4.87 |
| 2 | 0 | 0.77 | 9 | 7 | 9.54 |
| 2 | 7 | 3.58 | 9 | 14 | 15.36 |
| 2 | 14 | 6.58 | 10 | 0 | 5.82 |
| 3 | 0 | 1.20 | 10 | 7 | 11.15 |
| 3 | 7 | 4.15 | 10 | 14 | 18.21 |
| 3 | 14 | 7.34 | 11 | 0 | 6.95 |
| 4 | 0 | 1.67 | 11 | 7 | 13.28 |
| 4 | 7 | 4.70 | 11 | 14 | 22.49 |
| 4 | 14 | 8.19 | 12 | 0 | 8.39 |
| 5 | 0 | 2.18 | 12 | 7 | 16.39 |
| 5 | 7 | 5.49 | 12 | 14 | 30.10 |
| 5 | 14 | 9.16 | 13 | 0 | 10.32 |
| 6 | 0 | 2.74 | 13 | 7 | 21.94 |
| 6 | 7 | 6.28 | 13 | 14 | 48.70 |
| 6 | 14 | 10.28 | 14 | 0 | 13.32 |
| 7 | 0 | 3.36 | 14 | 7 | 39.01 |
| 7 | 7 | 7.19 | 14 | 13 | 146.61 |
| 7 | 14 | 11.62 | 14 | 14 | >146.61 |

The foregoing Table contains only selected portions of the entire Table, which includes all combinations possible from 0–0 to 14—14.

EXAMPLE NO. 4

Three cassettes D1, D2 and D3 each having 14 wells 54 of 0.180 ml. and 14 wells 56 of 0.018 ml. volume were loaded with a lagoon sample as follows: cassette D1 was loaded with undiluted sample, cassette D2 was loaded with a 10-fold dilution of the sample, and cassette D3 was loaded with a 100-fold dilution of the sample. After incubation at 35° C. for 18 hours the following results are obtained:

Cassette D1 contained 14 positive large wells 54 and 14 positive small wells 56, indicating the concentration to be greater than 146 cells per ml. Cassette D2 showed 12 large wells 54 positive and 7 small wells 56 positive. From Table B this combination was found to equate to 16.39 cells per ml. Since a 10-fold dilution was used, the count in the original sample was 163.9 cells per ml. The third cassette D3 showed 4 positive large wells 54 and no positive small wells 56. From Table B this combination equated to 1.67 cells per ml. But since a 100-fold dilution was used, the actual count in the original sample is 100 × 1.67 or 167 cells per ml.

FURTHER MODIFICATION

A modified cassette E provides a three fold dilution, thus increasing still further the range of concentration over which the cassette E remains functional. The cassette E includes a plate 70 which on one of its major surface areas is stepped so that plate contains a thick segment 72 and a thin segment 74.

The thick segment 72 contains five large wells 76 which are arranged in a row and extend completely through the thick segment 72. The large wells 76 are of equal volume, which may be 0.5 ml. All of the large wells 76 are tied together through a major feeder channel 78 having lateral branch channels 80 leading therefrom into the large wells 76. The major feeder channel 78 near its mid-portion communicates with a bore 82 which opens out of the side edge extended along the thick segment 72 of the plate 70. The bore 82 contains a septum 84 which is fitted tightly therein.

The thin segment 74 contains a plurality of intermediate wells 86 which are arranged in two rows therein parallel to the row of large wells 76. Successive intermediate wells 86 are located in different rows. Each intermediate well extends completely through the thin segment 74 and may possess a volume of 0.05 ml.

The intermediate wells 86 are arranged in groups of five, and each group of five is connected with a single large well 76 through a short discharge channel 88, a secondary feeder channel 90, and individual supply channels 92 which branch off of the secondary feeder channel 90. The channels 88, 90 and 92 open out of the uninterrupted surface of the plate 70, that is the surface located opposite from the stepped surface out of which the channels 78 and 80 open.

The thin segment 74 further contains small wells 94 which likewise extend entirely through the thin segment 74, but are considerably smaller in diameter than the intermediate wells 86. Indeed, the small wells 94 may have a volume of only 0.005 ml. Each small well 94 is connected with a different intermediate well 86 through a filler channel 96 which opens out of the stepped surface of the plate 70.

Located beyond each small well 94 is an overflow well 98, and each overflow well 98 is connected with its small well 94 through a short connecting channel 100 which opens out of the uninterrupted surface of the plate 70.

Both are uninterrupted surface and the step surface of the plate 70 are covered with tapes 102 which close the ends of the wells 76, 86 and 94 as well as the sides of the channels 78, 80, 88, 90, 92, 96 and 100.

In use, the cassette E is filled with a mixture of speciment and liquid culture medium by utilizing a loading device quite similar to the loading device L. In other words, the cassette E is loaded by evacuating air from the interior thereof and then replacing the evacuated air with a mixture of specimen and liquid nutrient medium. The nutrient medium is not contained within the wells 76, 86 and 94 themselves, but constitutes a broth into which the specimen is diluted. This procedure is utilized inasmuch as it is difficult to contain the proper amount of dried medium in the large wells 76 since there is a tendency for such medium to wash through into the intermediate wells 86 and the small wells 94. This would provide too great of concentration of culture medium in the intermediate and small wells 86 and 94 and too small a concentration in the large wells 76. However, by locating each well 76, 86 and 94 at the end of its own filling channel as in the cassettes C and D, it is possible to use a dehydrated culture medium in each well 76, 86 and 94 of the cassette E.

The cassette E, once it is loaded, is incubated and then observed in the manner of the cassettes C and D. Since the cassette E in effect provides a three fold was diluted 100 times, the concentration of the sample was 616 cells per ml.

The cassette E3 containing the sewage effluent had five positive large wells 76, 16 positive intermediate wells 86, and no positive small wells 94. This amounted to a concentration of 17.44 cells per ml. within the cassette E3 itself, and since the sample was diluted 100 times by the culture medium, the actual concentration in the sample amounted to 1,744 cells per ml.

TABLE C

For a 55 well cassette containing 5 wells of 0.5 ml., 25 wells of 0.05 ml. and 25 wells of 0.005 ml. Only selected portions of entire table are presented.

| Number Positive | | | MPN | Number Positive | | | MPN |
| --- | --- | --- | --- | --- | --- | --- | --- |
| 0.5 ml | 0.05 ml | 0.005 ml | (cells/ml) | 0.5 ml | 0.05 ml | 0.005 ml | (cells/ml) |
| 0 | 0 | 0 | <0.25 | 3 | 4 | 4 | 3.95 |
| 1 | 0 | 0 | .27 | 3 | 8 | 8 | 7.59 |
| 1 | 1 | 0 | .55 | 3 | 16 | 0 | 8.31 |
| 1 | 1 | 1 | .83 | 3 | 16 | 25 | 22.30 |
| 1 | 2 | 0 | .84 | 4 | 0 | 0 | 1.45 |
| 1 | 4 | 0 | 1.43 | 4 | 1 | 0 | 1.85 |
| 1 | 4 | 4 | 2.60 | 4 | 1 | 1 | 2.25 |
| 1 | 8 | 8 | 5.15 | 4 | 2 | 0 | 2.27 |
| 1 | 16 | 0 | 5.47 | 4 | 4 | 0 | 3.17 |
| 1 | 16 | 25 | 14.31 | 4 | 4 | 4 | 5.04 |
| 2 | 0 | 0 | 0.59 | 4 | 8 | 8 | 9.85 |
| 2 | 1 | 0 | 0.90 | 4 | 16 | 0 | 11.18 |
| 2 | 1 | 1 | 1.21 | 4 | 16 | 25 | 31.28 |
| 2 | 2 | 0 | 1.22 | 5 | 0 | 0 | 2.07 |
| 2 | 4 | 0 | 1.87 | 5 | 1 | 0 | 2.56 |
| 2 | 4 | 4 | 3.19 | 5 | 1 | 1 | 3.05 |
| 2 | 8 | 8 | 6.16 | 5 | 2 | 0 | 3.09 |
| 2 | 16 | 0 | 6.60 | 5 | 4 | 0 | 4.27 |
| 2 | 16 | 25 | 17.40 | 5 | 4 | 4 | 6.81 |
| 3 | 0 | 0 | .97 | 5 | 8 | 0 | 7.29 |
| 3 | 1 | 0 | 1.32 | 5 | 16 | 0 | 17.44 |
| 3 | 1 | 1 | 1.67 | 5 | 16 | 25 | 54.95 |
| 3 | 2 | 0 | 1.68 | 5 | 25 | 24 | 643.77 |
| 3 | 4 | 0 | 2.43 | 5 | 25 | 25 | >643.77 | dilution, the range of concentration through which the cassette E is functional is quite broad.

EXAMPLE NO. 5

Three cassettes E1, E2 and E3 have large wells 76, intermediate wells 86 and small wells 94 of 0.5 ml., 0.05 ml., and 0.005 ml. respectively. From a statistical standpoint, this gives the cassettes an effective range of 0.258 to 643.77 cells per ml. (see Table C).

Into the cassette E1 was loaded a sample derived by mixing 10 ml. of drinking fountain water with 10 ml. of double strength universal medium. Another mixture was prepared by mixing 1 ml. of a lagoon sample with 100 ml. of single strength medium and that mixture was vacuum loaded into the cassette E2. Likewise, 1 ml. of the sewage effluent is mixed with 100 ml. of single strength universal medium and that mixture is loaded into the cassette E3. All three cassettes E1, E2 and E3 were incubated.

The cassette E1 showed one positive large well 76, but no positive intermediate wells 86 or small wells 94. From the following Table C, it was determined that the concentration in the mixture within the cassette E1 was 0.27 cells per ml. but since drinking sample was diluted in an equal volume of diluent, the concentration in the actual water sample was 2 × 0.27 or 0.54 cells per ml.

The cassette E2 had two positive large wells 76, 8 positive intermediate wells 86, and 8 positive small wells 94. From the Table C it was determined that the concentration of the mixture in the cassette E2 amounted to 6.16 cells per ml., but since the sample The foregoing Table includes only a selected number of examples from the actual table, which includes all possible combinations from 0–0–0 to 5–25–25.

FURTHER CONSIDERATIONS

The cassettes C, D and E may be observed during incubation by the naked eye, in which case turbidity, color change or some other change in the light transmitting characteristics of the wells is clearly visible. On the other hand, the cassettes C and D may be monitored electro-optically during the incubation period for changes in the optical density of the wells 54 and 56. An electro-optical detector which projects light through the wells, measures the intensity of the light leaving the wells, and records that intensity in graphic form as a function of time, is disclosed in U.S. Pat. No. 3,963,355, previously referred to herein.

Where wells of different volume are employed such as in the cassettes D and E, the volumes need not be related by factors of 10. For example, in the cassette D the small cells 56 may be 1/20 the volume of the large cells 54. This is easily achieved in the cassette D by extending the small cells 56 only half way through the plate 50 instead of entirely through it.

Tables A, B and C were derived from statistical computations prepared much in the same manner as MPN Tables are formulated.

This invention is intended to cover all changes and modifications of the example of the invention herein chosen for purposes of the disclosure which do not constitute departures from the spirit and scope of the invention.

What is claimed is:

1. An apparatus for determining the concentration of microorganisms in a water specimen, said apparatus comprising a rigid body having a plurality of first wells and a plurality of second wells therein, the first wells being of equal volume and the second wells being of equal volume with the volume of the second wells being different from that of the first wells, the rigid body also having an inlet which opens outwardly from the body and forms an entry into which the water specimen may be introduced into the body, the rigid body further having filling channels leading up to and opening into the first and second wells, there being a separate filling channel for each first well and for each second well with each filling channel communicating with the inlet such that a water specimen introduced into the inlet passes into the filling channels and then into the wells, the upstream end of each filling channel being in communication with the inlet independently of the other filling channels so that the water specimen will flow into each well without passing through another well; means closing the ends of the wells and the sides of the filling channels for isolating the interiors of the wells and filling channels from the surrounding atmosphere except through the inlet, said means being transparent; and a culture medium in the wells.

2. An apparatus according to claim 1 and further comprising means at the inlet for isolating the channels from the surrounding atmosphere.

3. An apparatus according to claim 2 wherein the means at the inlet for isolating the channels comprises a septum in the inlet of the rigid body.

4. An apparatus according to claim 1 wherein the means for closing the ends of the wells is a light-transmitting tape adhered to those surface areas of the rigid body out of which the wells open.

5. A process for ascertaining the concentration of microorganisms in a water specimen, said process comprising: placing the water specimen in communication with filling channels leading to sealed first cavities which are of known and equal volume; placing the water specimen in communication with additional filling channels leading to sealed second cavities which are of known and equal volume, the volume of the second cavities being less than the volume of the first cavities; placing the water specimen under a vacuum so that air is evacuated from the first and second cavities and filling channels through the water specimen; releasing the vacuum and subjecting the water specimen to atmospheric pressure so that the water specimen is forced through the filling channels and into the first and second cavities to take the place of the evacuated air; mixing the water specimen with a nutrient medium such that a mixture of water specimen and nutrient medium exists in the first and second cavities; observing the water specimen in the first and second cavities for a change in the appearance thereof to determine the number of cavities which change appearance, and comparing the number of cavities which do change appearance with tabulated results derived from statistical evaluations to determine the concentration of microorganisms.

6. A process according to claim 5 wherein the water specimen and nutrient medium are mixed together in the first and second cavities.

7. A process according to claim 5 and further comprising placing the water specimen in communication with third cavities which are of known and equal volume, the volume of the third cavities being less than the volume of the second cavities, whereby when the water specimen is placed under a vacuum, the air is evacuated from the third cavities as well as from the first and second cavities, and when the vacuum is thereafter released, the water specimen is forced into the third cavities, and comparing the number of third cavities which change appearance with tabulated results derived from statistical evaluations to determine the concentration of microorganisms; and wherein the step of mixing the water specimen with the nutrient medium is such that a mixture of water specimen and nutrient medium also exists in the third cavities.

* * * * *